United States Patent [19]

Sauter et al.

[11] Patent Number: 5,346,909
[45] Date of Patent: Sep. 13, 1994

[54] FUNGICIDAL COMPOSITION

[75] Inventors: Hubert Sauter, Mannheim; Klaus Schelberger, Goennheim; Reinhold Saur, Boehl-Iggelheim; Gisela Lorenz, Neustadt; Eberhard Ammermann, Heppenheim, all of Fed. Rep. of Germany

[73] Assignee: BASF Aktiengesellschaft, Ludwigshafen, Fed. Rep. of Germany

[21] Appl. No.: 136,035

[22] Filed: Oct. 14, 1993

Related U.S. Application Data

[62] Division of Ser. No. 25,577, Mar. 3, 1993, Pat. No. 5,286,724, which is a division of Ser. No. 904,654, Jun. 26, 1992, Pat. No. 5,242,920.

[30] Foreign Application Priority Data

Jul. 22, 1991 [DE] Fed. Rep. of Germany ....... 4124255

[51] Int. Cl.$^5$ .................... A01N 43/40; A01N 37/12
[52] U.S. Cl. .................... 514/317; 514/539; 514/239.5; 514/231.2
[58] Field of Search ................ 514/317, 539

[56] References Cited
U.S. PATENT DOCUMENTS 4,829,085  5/1989  Wenderoth et al. ............. 514/522

Primary Examiner—Glennon H. Hollrah
Assistant Examiner—Brian M. Burn
Attorney, Agent, or Firm—Oblon, Spivak, McClelland, Maier & Neustadt

[57] ABSTRACT

A fungicidal composition of
  a) methyl α-methoximino-2-[(2-methylphenoxy)-methyl]-phenylacetate

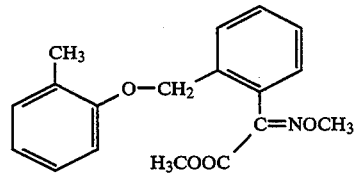

and
  b) 4-(2-methyl-3-[4-tert-butylphenyl]-propyl)-2,6-dimethylmorpholine (fenpropimorph)

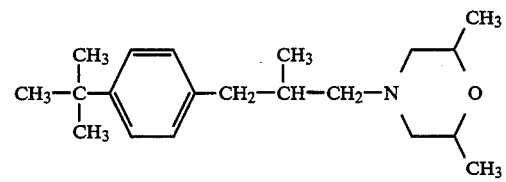

or the active ingredient tridemorph or the active ingredient fenpropidin,
and methods of combating fungi with this composition.

8 Claims, No Drawings

FUNGICIDAL COMPOSITION

This is a division of application Ser. No. 08/025,577, filed on Mar. 3, 1993, now U.S. Pat. No. 5,286,724, which is a division of application Ser. No. 07/904,654, filed on Jun. 26, 1992, now U.S. Pat. No. 5,242,920.

The present invention relates to fungicidal compositions having a synergistic fungicidal action, and to methods of combating fungi with these compositions.

It is known to use methyl α-methoximino-2-[(2-methylphenoxy)-methyl]phenylacetate

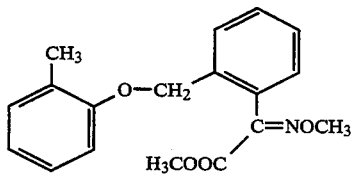

as a fungicide (EP 253,213). It is also known to use the active ingredient 4-(2-methyl-3-[4-tert-butylphenyl]-propyl)-2,6-dimethylmorpholine

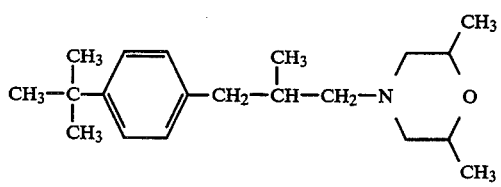

and the active ingredients tridemorph and fenpropidin and their salts as fungicides (DE 26 56 747).

We have now found that a composition of
a) methyl α-methoximino-2-[(2-methylphenoxy)-methyl]-phenylacetate

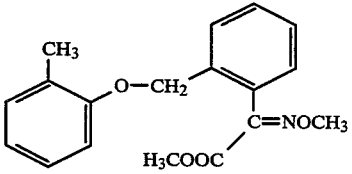

and
b) 4-(2-methyl-3-[4-tert-butylphenyl]-propyl)-2,6-dimethylmorpholine (fenpropimorph)

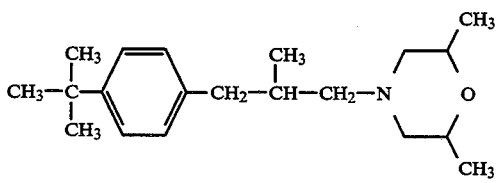

or the active ingredient tridemorph or the active ingredient fenpropidin
has a synergistic fungicidal action. The mixture ratio (by weight) of compounds a) and b) is such that a synergistic fungicidal action occurs, for example a ratio of a):b) of from 5:1 to 1:5, especially from 3:1 to 1:3, and preferably from 2:1 to 1:2. The synergistic effect of the composition is apparent from the fact that the fungicidal action of the composition of a)+b) is greater than the sum of the fungicidal actions of a) and b).

Component a) may be present in two stereoisomer forms because of the —C=N double bond. The (E) isomer is preferred.

The invention embraces compositions containing pure isomers of compound a), especially the (E) isomer, and compositions containing mixtures of isomers.

The component fenpropimorph may be present in two stereoisomer forms (morpholine ring), the cis isomer being preferred.

The invention embraces compositions containing pure isomers of the compound fenpropimorph, especially the cis isomer, and compositions containing mixtures of isomers.

Preferred compositions are those which contain component a) predominantly in the form of the (E1 isomer, and component b) predominantly as the cis isomer:

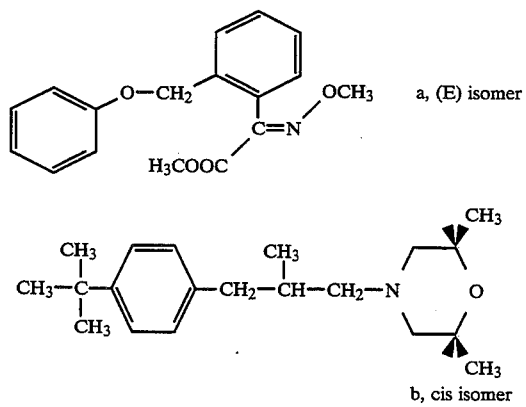

The active ingredient fenpropimorph b) may also be present in the form of its salts. These compositions too are embraced by the invention.

Salts are produced by reaction with acids, e.g., hydrohalic acids such as hydrofluoric acid, hydrochloric acid, hydrobromic acid or hydroiodic acid, or sulfuric acid, phosphoric acid, nitric acid or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid and 1,2-naphthalenedisulfonic acid.

Usually, the pure active ingredients a) and b) are advantageously used, to which other active ingredients such as insecticides, acaricides, nematicides, herbicides, other fungicides, growth regulators and/or fertilizers may be added.

The fungicidal compositions according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the composition according to the invention as possible.

Normally, the plants are sprayed or dusted with the compositions, or the seeds of the plants are treated with the compositions.

The formulations are prepared in known manner, e.g., by extending the composition with solvents and/or carriers, if desired using emulsifiers and dispersants; if water is employed as diluent, other organic solvents may also be used as auxiliary solvents. Examples of suitable auxiliaries are essentially solvents such as aromatics (e.g., xylene), chlorinated aromatics (e.g., chlorobenzenes), paraffins (e.g., petroleum fractions), alcohols (e.g., methanol, butanol), ketones (e.g., cyclohexanone), amines (e.g., ethanolamine, dimethylformamide), and water; carriers such as natural rock flours (e.g., kaolins, clays, talc and chalk), and synthetic rock flours (e.g., highly disperse silicic acid, silicates); emulsifiers such as nonionic and anionic emulsifiers (e.g., polyoxyethylene fatty alcohol ethers, alkyl sulfonates and aryl sulfonates), and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The compositions are extremely effective on a broad spectrum of phytopathogenic fungi, in particular those from the class consisting of the Ascomycetes and Basidiomycetes. Some of them have a systemic action and can be used as foliar and soil fungicides.

The compositions are of particular interest for controlling a large number of fungi in various crops or their seeds, especially wheat, rye, barley, oats, rice, Indian corn, lawns, cotton, soybeans, coffee, sugar cane, grapes and other fruit, and ornamentals, and in vegetables such as cucumbers, beans and cucurbits, and the seeds of these plants.

The compositions are applied by treating the fungi, or the seed, plants or materials to be protected against fungus attack, or the soil with a fungicidally effective amount of them.

The compositions may be applied before or after infection of the materials, plants or seed by the fungi.

The compositions are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Rhynchosporium in cereals,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and verticillium species in various plants,
Plasmopara viticola in grapes,
Alternaria species in fruit and vegetables.

The novel compositions may also be used for protecting materials (timber), e.g., against Paecilomyces variotii.

The fungicidal agents generally contain from 0.1 to 95, and preferably from 0.5 to 90, wt % of active ingredient.

The application rates of the compositions according to the invention depend on the effect desired, and range from 0.01 to 3 Kg of active ingredient composition per hectare.

When the compositions are used for treating seed, application rates of from 0.001 to 50, and preferably from 0.01 to 10, g per Kg of seed are generally required.

EXAMPLE 1

Eradicative action on wheat mildew

Wheat plants of the "Kanzler" variety were treated, after they had developed 3 leaves, in one experiment with wheat mildew (Erysiphe graminis vat. tritici) which was unsusceptible to fungicides containing a triazole radical in the molecule, and in a further experiment with wheat mildew which was susceptible to fungicides containing a triazole radical in the molecule, and were treated, after fungus attack had developed on 5% of the leaf surface, with the stated concentrations of aqueous formulations of the active ingredients. The amount of water corresponded to 400 liters/ha. The plants were cultivated in the greenhouse for 20 days at 18° to 22° C. The leaf area under fungus attack was then assessed in percent. These figures were then converted into degrees of action. The degree of action in the untreated control was set at 0. The degree of action when 0% of the leaf area was attacked by fungus was set at 100. The expected degrees of action of the active ingredient composition were determined in accordance with the Colby formula (Colby, S. R., "Calculating synergistic and antagonistic responses of herbicide combinations", Weeds, 15, pp. 20-22, 1967) and compared with the degrees of action observed.

The values for the fungicidal action varied between the individual experiments because the plants in the individual experiments exhibited varying degrees of attack; for this reason, only the results within the same experiment can be compared with each other.

Colby formula $E = x + y - \frac{x \cdot y}{100}$

E = expected degree of action, expressed in % of the untreated control, when active ingredients A and B are used in concentrations of m and n x = degree of action, expressed in % of the untreated control, when active ingredient A is used in a concentration of m y = degree of action, expressed in % of the untreated control, when active ingredient B is used in a concentration of n Active ingredient
I. Methyl-α-methoximino-2-[(2-methylphenyl)-oxymethyl]-phenylacetate

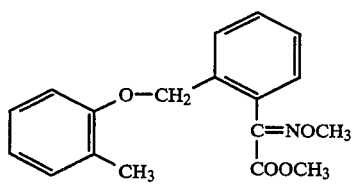

II. Fenpropimorph, 4-[3-(4-tert.-butylphenyul)-2-methylpropyl]-cis-2,6-dimethylmorpholine

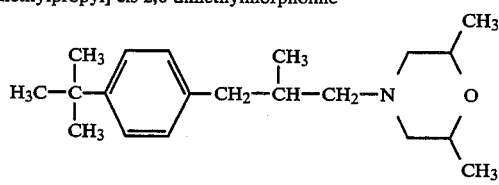

III. Fenpropidin, N-[3-(4-tert.-butylphenyl)-2-methylpropyl]-piperidine

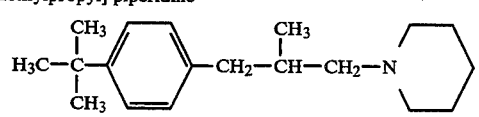

IV. Tridemorph, N-tridecyl-2,6-dimethyl-morpholine

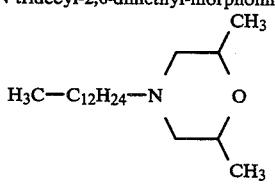

Experiment 1:
Eradicative action on Erysiphe graminis in wheat (Erysiphe graminis triazole-resistant)

| Active ingredient | Active ingredient conc. in spray liquor in % | Degree of action in % of untreated control |
|---|---|---|
| Control (untreated) | — | 0 |
| I. | 0.05 | 40 |
| II. Fenpropimorph | 0.05 | 20 |
| III. Fenpropidin | 0.05 | 23 |
| IV. Tridemorph | 0.05 | 13 |
| Composition acc. to invention | | |
| I. + II.  Ratio 1:3  0.01 + 0.03 | | 83 |
| I. + III. Ratio 1:3  0.01 + 0.03 | | 89 |
| I. + IV.  Ratio 1:3  0.01 + 0.03 | | 67 |

The results show that 0.04% (0.01+0.03) of the composition has a better fungicidal action than 0.05% of the individual active ingredients.

The same experiment with triazole-susceptible Erysiphe graminis confirmed the above results.

Experiment 2:
Eradicative action on Erysiphe graminis in wheat (Erysiphe graminis triazole-resistant)

| Active ingredient | Active ingredient conc. in spray liquor in % | Degree of action in % of untreated control |
|---|---|---|
| Control (untreated) | — | 0 |
| I. Active ingredient | 0.1 | 65 |
|  | 0.001 | 21 |
| II. Fenpropimorph | 0.1 | 52 |
|  | 0.01 | 11 |

| Composition acc. to invention | Degree of action observed | Degree of action calculated*) |
|---|---|---|
| I + II  0.01 + 0.01  Ratio 1:1 | 55 | 29.7 |
| I + II  0.1 + 0.1  Ratio 1:1 | 100 | 83.2 |
| I + II  0.1 + 0.01  Ratio 10:1 | 87 | 68.8 |
| I + II  0.01 + 0.1  Ratio 1:10 | 79 | 62.1 |

*)Calculated by the Colby formula

The same experiment with triazole-susceptible Erysiphe graminis confirmed the above results.

What we claim is:
1. A fungicidal composition comprising a synergistically fungicidally effective amount of a composition of
  a: methyl α-methoximino-2-[(2-methylphenoxy)-methyl]-phenylacetate of the formula

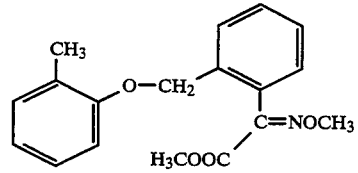

and
  b: N-[3-(4-tert.-butylphenyl)-2-methylpropyl]-piperidine

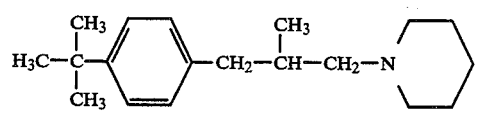

in a ratio of a:b from 5:1 to 1:5.

2. A method for combating fungi, comprising the step of applying a synergistically fungicidally effective amount of a composition of claim 1 to the fungi or to seeds, plants or materials subject to fungal attack.

3. A fungicidal composition of claim 1, wherein the weight ratio of a:b is from 3:1 to 1:3.

4. A fungicidal method according to claim 2, wherein the weight ratio of a:b is from 3:1 to 1:3.

5. A fungicidal composition of claim 1, wherein the weight ratio of a:b is from 1:2 to 2:1.

6. A fungicidal method according to claim 2, wherein the weight ratio of a:b is from 1:2 to 2:1.

7. A fungicidal agent containing a synergistically fungicidally effective amount of a composition of
   a) methyl α-methoximino-2-[(2-methylphenoxy)methyl]phenylacetate

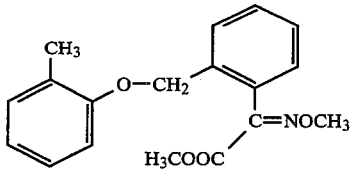

and
   b) N-[3-(4-tert.-butylphenyl)-2-methylpropyl]-piperidine

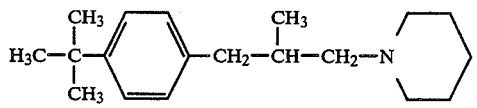

in a ratio of a:b of about 1:3.

8. A process for combating fungi, comprising contacting fungi or the materials, areas, plants, or seeds threatened by fungus attack with a synergistically fungicidally effective amount of a composition of
   a) methyl α-methoximino-2-[(2-methylphenoxy)methyl]phenylacetate

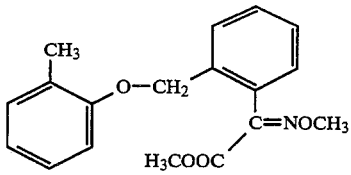

and
   b) N-[3-(4-tert.-butylphenyl)-2-methylpropyl]-piperidine

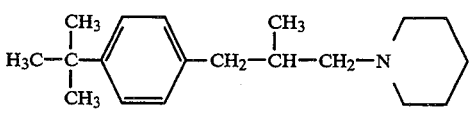

in a ratio of a:b of about 1:3.

* * * * *